US00PP13708P39

(12) United States Plant Patent
Scheffers

(10) Patent No.: US PP13,708 P3
(45) Date of Patent: Apr. 1, 2003

(54) DRACAENA PLANT NAMED '0103GJ'

(76) Inventor: Ruud A. M. Scheffers, Plaats 9, 2675 CK Honselersdijk (NL)

( * ) Notice: Subject to any disclaimer, the term of this patent is extended or adjusted under 35 U.S.C. 154(b) by 0 days.

(21) Appl. No.: 09/962,120

(22) Filed: Sep. 26, 2001

(65) Prior Publication Data

US 2002/0120969 P1 Aug. 29, 2002

(30) Foreign Application Priority Data

Feb. 26, 2001 (EP) ..... 2001/0357

(51) Int. Cl.[7] ..... A01H 5/00

(52) U.S. Cl. ..... Plt./383

(58) Field of Search ..... Plt./383

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named '0103GJ' characterized by its compact plant habit, fast growth rate; leaves which are straight with straight tips; and upright growth of green leaves, RHS 139 A.

2 Drawing Sheets

LATIN NAME OF THE GENUS AND SPECIES OF THE PLANT CLAIMED

*Dracaena Vand. Ex. L. fragrans* (group Compacta).

VARIETY DENOMINATION

'0103GJ'.

BACKGROUND OF THE INVENTION

The present invention comprises a new and distinct cultivar of Dracaena plant botanically known as *Dracaena Vand. Ex. L. fragrans* (group Compacta) and hereinafter referred to by the cultivar name '0103GJ'.

The new cultivar was selected by the inventor, Ruud A. M. Scheffers, in Honselersdijk, The Netherlands, in January 1998. The new cultivar was obtained as a natural mutation of *Dracaena Vand. Ex. L. fragrans* (group Compacta) 'White Jewel' (U.S. Plant Pat. No. 12,433).

The new cultivar was first asexually propagated by the inventor in Honselersdijk, The Netherlands, in May 1998. Subsequent asexual reproduction of the new cultivar by division has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish '0103GJ' as a new and distinct cultivar:

1. fast growth rate, mature plant growth approximately 20 weeks from the planting of a rooted cutting;
2. the upright growth of the green leaves, RHS 139 A;
3. the straight leaf tips; and
4. compact growth habit;

'0103GJ' has not been observed under all possible environmental conditions. The phenotype on the new cultivar may vary significantly with variations in environment such as temperature, light intensity, and day length without any change in genotype. The following observations, measurements and values describe plants grown in Honselersdijk, The Netherlands under greenhouse conditions which closely approximate those generally used in horticultural practice.

In comparison with the well-known Dracaena cultivar 'Janet Craig Compacta' (unpatented), '0103GJ' has much shorter leaves, grows much more compact, has straight leaves ('Janet Craig' has hanging tips), while its leaves grow more upright. In comparison with the well-known Dracaena cultivar 'Janet Craig Compacta', '0103GJ' has much longer leaves, has straight leaves ('Janet Craig Compacta' has hanging tips) while its leaves grow less upright, and it grows less compact. In comparison with the well-known Dracaena cultivar 'White Jewel' (U.S. Plant patent application Ser. No. 09/326,615), '0103GJ' has green leaves while 'White Jewel' has variegated leaves.

BRIEF DESCRIPTION OF THE DRAWING

The accompanying photographs illustrate a 16-week old plant of Dracaena '0103GJ', with colors being as true as possible with illustrations of this type. The first drawing shows a 16-week old plant of Dracaena '0103GJ'. The second drawing shows a 16-week old plant (taken from a top-cutting) of Dracaena '0103GJ' together with a 16-week old plant (taken from tip-cutting) of Dracaena 'Janet Craig Compacta'.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Parentage: Mutant of Dracaena Vand. Ex. *L. fragrans* (group Compacta) 'White Jewel'.

Propagation: Primarily by vegetative division of the plant head or apical meristem.

General observations:

*Growing conditions.*—'0103GJ' is grown in a greenhouse. The grower propagates '0103GJ' in a normal commercial greenhouse under temperatures of 20–21 degrees Celsius day and night. As with most Dracaena varieties, '0103GJ' does not stand direct sunlight so sun shields are closed when sunlight becomes to bright. No artificial lighting or photoperiodic treatments are conducted. Highest temperature resistance is at least 40 degrees Celsius, lowest is 5 degrees Celsius. Resistance, tolerance and susceptibility to stresses, pathogens and pests is very good. Compound fertilizer is added to the soil. There are no other cultural or environmental treatments.

*Plant vigor.*—Good.

Plant habit:

*Growth rate.*—Fast, mature plant growth approximately 20 weeks from the planting of a rooted cutting.

*Form.*—Medium compact/slightly elongated.

*Plant height.*—35 cm.

*Plant width.*—45 cm.

Leaves:

*Form and size.*—Narrow, ensiform with parallel ribs in the length: approximately 35 cm in length and 5 cm in width, base is cuneate, tip is accuminate.

*Leaf arrangement.*—Spiral.

*Texture.*—Strong and leather-like.

*Veins.*—Green slightly lighter than leaf (RHS 137 B).

*Under side color.*—Green (RHS 137 A).

*Upper side color.*—Green (RHS 139 A).

*Margin.*—Entire and slightly curled.

*Thickness.*—Medium.

*Number.*—Approximately 30.

Flowers: No flowers observed to date.

Stem:

*Length.*—Short, approximately 3 cm.

*Diameter.*—1.5 cm and formed by bases of leaves.

*Color.*—White to green (RHS 155 C to RHS 139 A).

*Other.*—Strong.

Roots: Orange-brown (RHS 168 D) in color, it takes approximately 3 weeks to initiate roots and approximately 7 weeks are needed to produce a rooted liner.

Plant disease/insect tolerance: '0103GJ' has a very high resistance against diseases and a very high tolerance against insects.

Reproductive organs: No flowers observed to date.

I claim:

1. A new and distinct cultivar of Dracaena plant named '0103GJ', as described and illustrated herein.

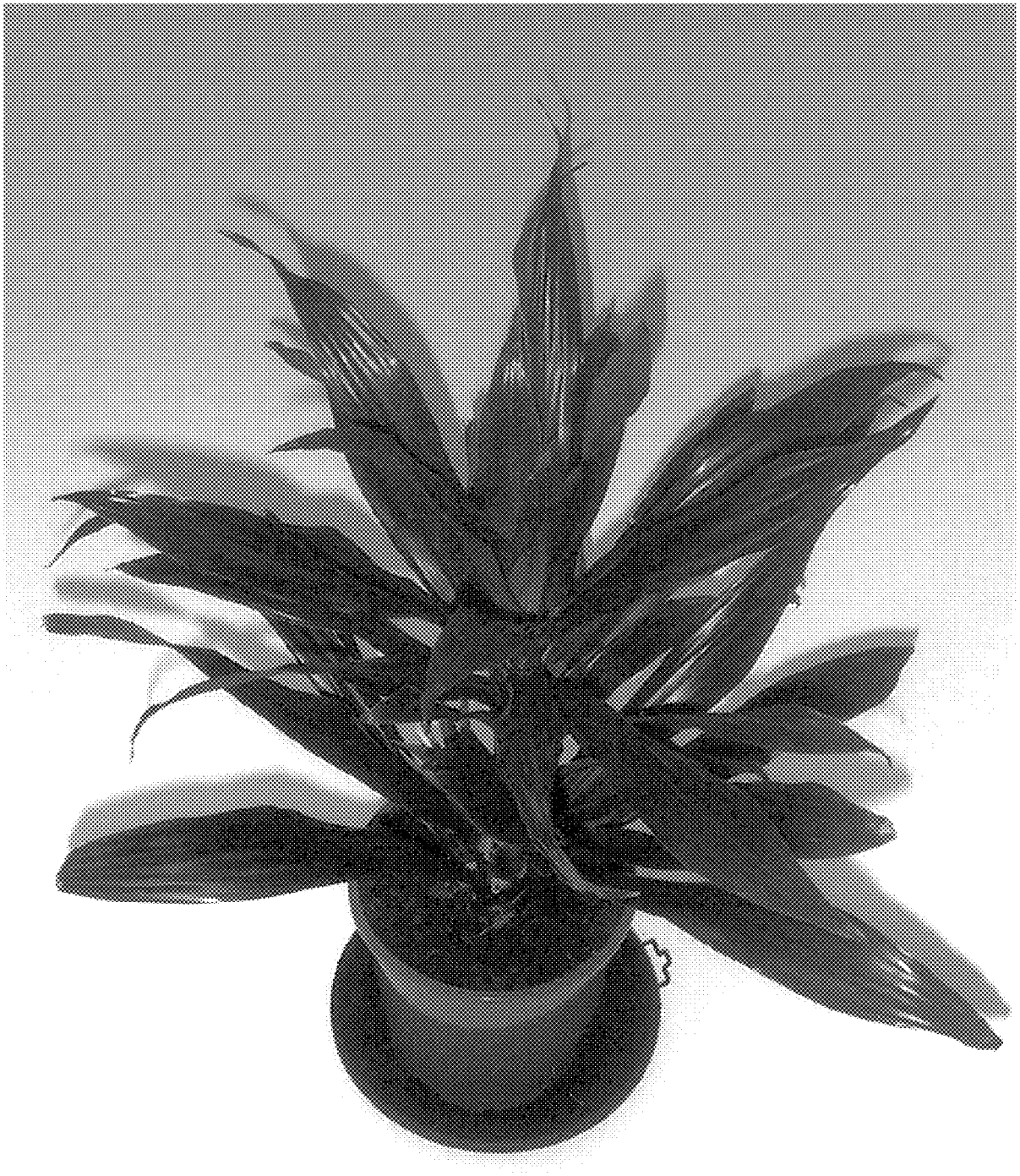

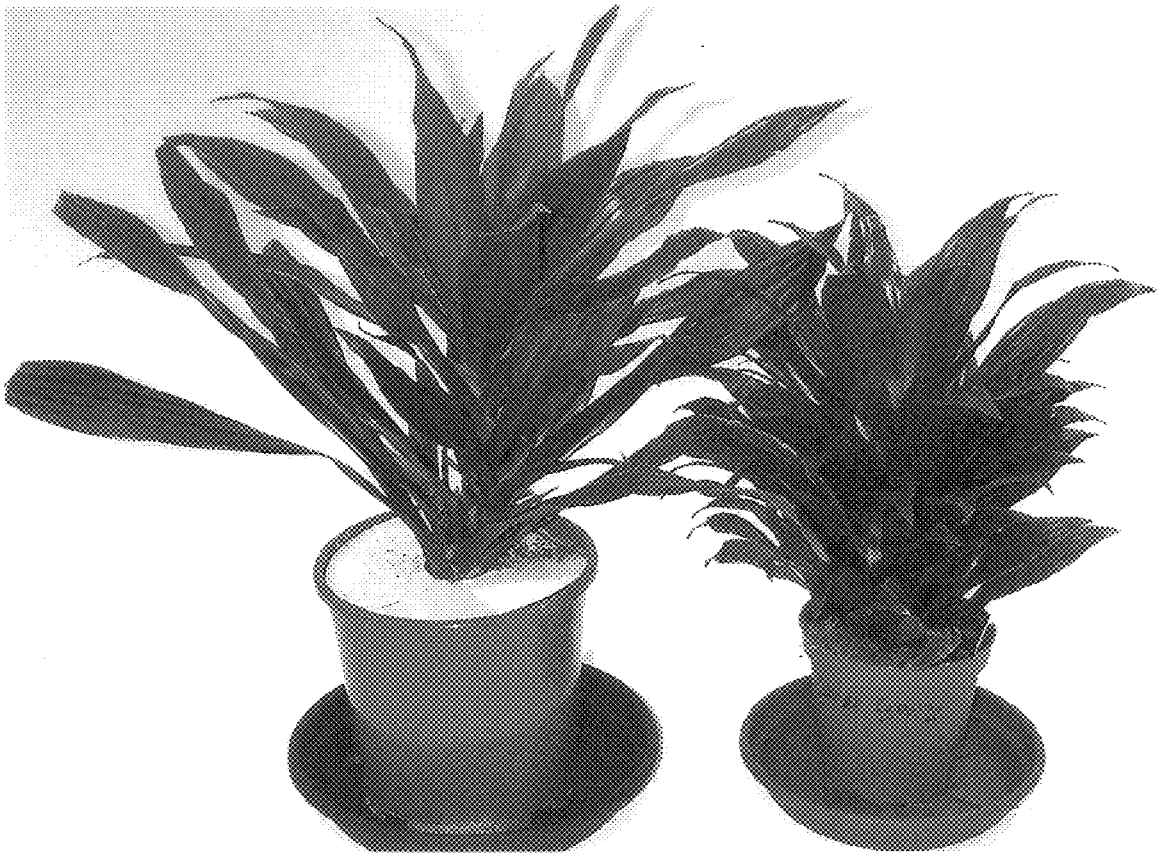

* * * * *